United States Patent [19]

Clough et al.

[11] Patent Number: 5,059,605
[45] Date of Patent: Oct. 22, 1991

[54] PYRIMIDINE DERIVATIVES USEFUL AS FUNGICIDES

[75] Inventors: John M. Clough, Marlow; Christopher R. A. Godfrey, Bracknell; Ian T. Streeting, Wokingham, all of United Kingdom

[73] Assignee: Imperial Chemical Industries plC, London, England

[21] Appl. No.: 506,790

[22] Filed: Apr. 10, 1990

[30] Foreign Application Priority Data

Apr. 19, 1989 [GB] United Kingdom ............... 8908875

[51] Int. Cl.$^5$ ................ A61K 31/505; A61K 31/535; C07D 401/12; C07D 401/14
[52] U.S. Cl. ..................................... 514/269; 514/63; 514/230.5; 514/248; 514/249; 514/258; 514/259; 514/272; 514/274; 514/255; 544/69; 544/105; 544/236; 544/279; 544/229; 544/298; 544/300; 544/310
[58] Field of Search .............. 544/300, 310, 298, 229, 544/69, 236, 105, 279; 514/272, 274, 269, 63, 230.5, 249, 248, 259, 258

[56] References Cited

FOREIGN PATENT DOCUMENTS 0242081 10/1987 European Pat. Off. ............ 544/298

Primary Examiner—Johann Richter
Attorney, Agent, or Firm—Cushman, Darby & Cushman

[57] ABSTRACT

Fungicidal compounds having the formula (I):

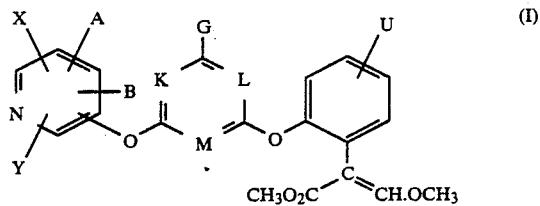

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^2$, $CO_2R^1$, $CONR^1R^2$, $CSNR^1R^2$, $CH_3O_2C.C:CH.OCH_3$, 1-(imidazol-1-yl)vinyl, a 5-membered heterocyclic ring containing one, two or three nitrogen heteroatoms, or a 5- or 6-membered heterocyclic ring containing one or two oxygen or sulphur heteroatoms, optionally a nitrogen heteroatom and optionally one or two oxo or thioxo substituents; or X and Y, when ortho to one another, join to form a 5- or 6-membered aliphatic or aromatic ring optionally containing one or two oxygen, sulphur or nitrogen atoms or one, two or three nitrogen or sulphur atoms; A, B, E, G and U are independently hydrogen, halogen, $C_{1-4}$ alkyl, $C_{1-4}$ alkoxy, cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one or more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano; and their pyridine N-oxides and N-alkyl pyridinium salts.

9 Claims, No Drawings

PYRIMIDINE DERIVATIVES USEFUL AS FUNGICIDES

This invention relates to derivatives of propenoic acid useful as fungicides, to processes for preparing them, to fungicidal compositions containing them, and to methods of using them to combat fungi, especially fungal infections of plants.

A range of pesticidal alkyl 2-(substituted)pyridinyl- and pyrimidinyloxyphenyl-3-alkoxypropenoates is described in EP-A-0242081.

According to the present invention there are provided compounds having the formula (I):

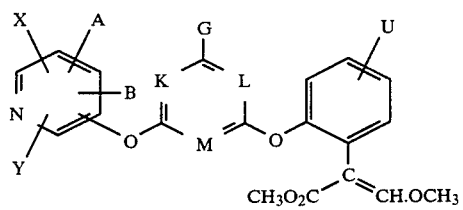

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $Nr^1R^2$, $NR^1OR^2$, $N_3$, $NHCOR^1$, $Nr^1CO_2R^2$, $NHCONR^1R^2$, $N=CHNR^1R^2$, $NHSO_2R^1$, $Or^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C:CH.OCH_3$, 1-(imidazol-1-yl)vinyl, a 5- membered heterocyclic ring containing one, two or three nitrogen heteroatoms, or a 5- or 6-membered heterocyclic ring containing one or two oxygen or sulphur heteroatoms, optionally a nitrogen heteroatom and optionally one or two oxo or thioxo substituents; or X and Y, when ortho to one another, join to form a 5- or 6-membered aliphatic or aromatic ring optionally containing one or two oxygen, sulphur or nitrogen atoms or one, two or three nitrogen or sulphur atoms; A, B, E, G and U are independently hydrogen, halogen (especially fluorine and chlorine), $C_{1-4}$ alkyl (especially methyl), $C_{1-4}$ alkoxy (especially methoxy), cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one or more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano; and their pyridine N-oxides and N-alkyl pyridinium salts.

Because of the unsymmetrically substituted double bond of the propenoate group, the compounds of the invention may be obtained in the form of mixtures of (E) and (Z) geometric isomers. However, these mixtures can be separated into individual isomers, and this invention embraces such isomers and mixtures thereof in all proportions including those which consist substantially of the (Z)-isomer and those which consist substantially of the (E)-isomer.

The (E)-isomer, in which the groups —$CO_2CH_3$ and —$OCH_3$ are on opposite sides of the olefinic bond of the propenoate group, are the more fungicidally active and form a preferred embodiment of the invention.

Alkyl groups contain from 1 to 4 carbon atoms and may be in the form of straight or branched chains. Examples are methyl, ethyl, (E)-propyl, (E)-butyl and (E)t-butyl. Cycloalkyl groups contain from 3 to 6 cabon atoms and include cyclopropyl and cyclohexyl.

Alkenyl and alkynyl groups contain from 2 to 4 carbon atoms and may be in the form of straight or branched chains. Examples are ethenyl, allyl, methylallyl and propargyl.

Halogen is typically fluorine, chlorine or bromine. Substituted aliphatic moieties include, in particular, halo($C_{1-4}$)alkyl, halo($C_{1-4}$)alkoxy, halo- ($C_{1-4}$)alkylthio, $CH_2OR^1$, $CH_2SR^1$ and $CH_2NR^1R^2$, wherein $R^1$ and $R^2$ are H, $C_{1-4}$ alkyl or phenyl.

Typical optional substituents of phenyl moieties are fluorine, chlorine, methyl, methoxy, nitro and cyano.

The ring

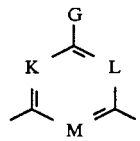

in formula (I) is a pyrimidine ring which may be joined to the phenoxy and pyridyloxy groups by any two of its ring carbon atoms adjacent to a ring nitrogen atom. The oxygen atom of the pyridyloxy group may be joined to any one of the pyridine ring carbon atoms.

Of particular interest are those compounds of formula (I) in which K and L are both nitrogen and M is CH. Typically, one or both of X and Y are hydrogen. When one of X and Y is not hydrogen it is preferably attached to the pyridine ring at the position adjacent to the oxygen link. A, B, G and U are all suitably hydrogen.

Thus, in one aspect, the invention provides compounds of formula (I) in which any two of K, L and M are nitrogen and the other is CH; A, B, G and U are all hydrogen; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $NR^1R^2$, $NHCOR^1$, $NHCONR^1R^2$, $NHSO_2R^1$, $OR^1$, $OCOR^1$, $OSO_2R^1$, $SR^1$, $SOR^1$, $SO_2R^1$, $COR^1$, $CR^1=NOR^2$, $CO_2R^1$, $CONR^1R^2$, $CSNR^1R^2$; or X and Y, when attached to C02R adjacent carbon atoms of the pyridine ring, join to form a 5- or 6-membered aliphatic or aromatic ring optionally containing one or more oxygen, sulphur or nitrogen atoms; and $R^1$ and $R^2$ are independently hydrogen, $C_{1-4}$ alkyl or phenyl; the aliphatic moieties of any of the foregoing being optionally substituted with one or more of halogen, cyano, $OR^1$ or $OCOR^1$ and the phenyl moieties of any of the foregoing being optionally substituted with one or more of halogen, $C_{1-4}$ alkyl, $C_{1-4}$ alkoxy, nitro or cyano; and their pyridine N-oxides and N-alkyl pyridinium salts.

In another aspect, the invention provides compounds of formula (I) in which two of K, L and M are nitrogen and the other is CH; A, B, G and U are all hydrogen; X, which is preferably attached to the pyridine ring at the position adjacent to the oxygen link, is hydrogen, halogen (e.g. fluorine, chlorine or bromine), $C_{1-4}$ alkyl (e.g. methyl or ethyl), $C_{1-4}$ alkyl (especially methyl) substituted with halogen (e.g. fluorine, chlorine or bromine), hydroxy, cyano, $C_{1-4}$ alkoxy (e.g. methoxy) or $C_{1-4}$ alkanoyloxy (e.g. acetoxy), $C_{2-4}$ alkenyl (e.g. ethenyl, allyl or methylallyl), $C_{2-4}$ alkynyl (e.g. ethynyl or propargyl), $C_{2-4}$ alkenyloxy (e.g. allyloxy), $C_{2-4}$ alkynyloxy (e.g. propargyloxy), phenyl, benzyloxy, cyano, isocyano, isothiocyanato, nitro, amino, mono- or di($C_{1-4}$)alkylamino (e.g. methylamino or dimethylamino), formylamino, $C_{1-4}$ alkanoylamino (e.g. acetamido), benzylamino, ureido, phenylureido, $C_{1-4}$ alkylsulphonylamino (e.g. mesylamino), phenylsulphonylamino, hydroxy, $C_{1-4}$ alkoxy (e.g. methoxy or ethoxy), phenoxy, $C_{1-4}$ alkanoyloxy (e.g. acetoxy), $C_{1-4}$ alkylsulphonyloxy (e.g. mesyloxy), phenylsulphonyloxy, $C_{1-4}$ alkylthio (e.g. methylthio), $C_{1-4}$ alkylsulphinyl (e.g. methylsulphinyl), $C_{1-4}$ alkylsulphonyl (e.g. mesyl and n-butylsulphonyl), formyl, $C_{1-4}$ alkanoyl (e.g. acetyl), benzoyl, hydroxyimino($C_{1-4}$)alkyl (e.g. hydroxyiminomethyl), $C_{1-4}$ alkoxyimino($C_{1-4}$)alkyl (e.g. methoxyiminomethyl), carbamoyl, $C_{1-4}$ alkylcarbamoyl (e.g. methylcarbamoyl), thiocarbamoyl or $C_{1-4}$ alkylthiocarbamoyl (e.g. methylthiocarbamoyl), the phenyl ring of any of the foregoing being optionally substituted with halogen (e.g. fluorine or chlorine), $C_{1-4}$ alkyl (e.g. methyl), $C_{1-4}$ alkoxy (e.g. methoxy), nitro or cyano; and Y is halogen (e.g. fluorine or chlorine), $C_{1-4}$ alkyl (e.g. methyl), $C_{1-4}$ alkoxy (e.g. methoxy), nitro, cyano or preferably, hydrogen. Alternatively to the above, X and Y, when (E) to one another, together form methylenedioxy, or together with the pyridine ring to which they are attached form a 9- or 10-membered ring system containing nitrogen, oxygen or sulphur heteroatoms. Examples of such ring systems include quinolines, isoquinolines, naphthyridines, pyranopyridines, pyridopyrazines, pyridopyridazines, pyridopyrimidines, pyridooxazines, and pyrrolo-, furo-, thieno-, triazolo- and thiadiazolopyridines.

In yet another aspect the invention provides compounds of the formula (I.1):

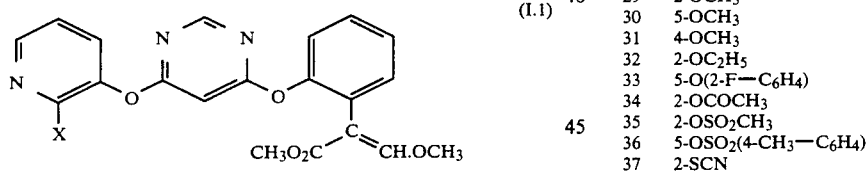

(I.1)

in which X is hydrogen, halogen (especially chlorine), $C_{1-4}$ alkyl (especially methyl), $C_{1-4}$ alkoxy (especially methoxy), $C_{1-4}$ alkylthio (especially methylthio), trifluoromethyl, trifluoromethoxy, cyano or nitro.

In yet another aspect the invention provides compounds of the formula (I.2):

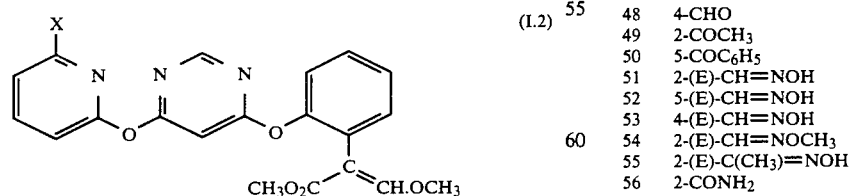

(I.2)

in which X is hydrogen, halogen (especially chlorine), $C_{1-4}$ alkyl (especially methyl), $C_{1-4}$ alkoxy, $C_{1-4}$ alkylthio, trifluoromethyl, trifluoromethoxy, cyano or nitro.

The invention is illustrated by the compounds listed in Tables I to IX which follow. Throughout these Tables the methyl 3-methoxypropenoate group has the (E)-configuration.

TABLE I

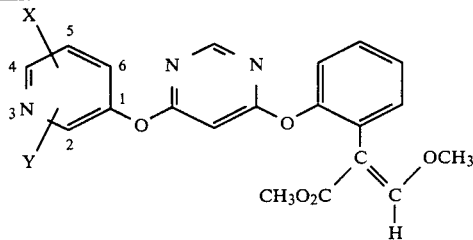

| Compound No. | X | Y | Melting Point (°C.) | Olefinic* |
|---|---|---|---|---|
| 1 | H | H | 135–6 | 7.47 |
| 2 | 2-F | H | | |
| 3 | 5-F | H | | |
| 4 | 4-F | H | | |
| 5 | 2-Cl | H | 104–5 | 7.49 |
| 6 | 5-Cl | H | | |
| 7 | 4-Cl | H | | |
| 8 | 2-Br | H | 98–9 | 7.49 |
| 9 | 2-CN | H | | |
| 10 | 5-CN | H | | |
| 11 | 4-CN | H | | |
| 12 | 2-NC | H | | |
| 13 | 2-NO$_2$ | H | 108–9 | 7.51 |
| 14 | 5-NO$_2$ | H | | |
| 15 | 4-NO$_2$ | H | | |
| 16 | 2-NH$_2$ | H | | |
| 17 | 5-NH(CH$_3$) | H | | |
| 18 | 2-N(CH$_3$)$_2$ | H | | |
| 19 | 2-NH.CHO | H | | |
| 20 | 2-NH.COCH$_3$ | H | | |
| 21 | 5-NH.COC$_6$H$_5$ | H | | |
| 22 | 2-NH.CONH$_2$ | H | | |
| 23 | 5-NH.CONH(C$_2$H$_5$) | H | | |
| 24 | 2-NH.SO$_2$CH$_3$ | H | | |
| 25 | 5-NH.SO$_2$C$_6$H$_5$ | H | | |
| 26 | 2-OH | H | | |
| 27 | 5-OH | H | | |
| 28 | 4-OH | H | | |
| 29 | 2-OCH$_3$ | H | | |
| 30 | 5-OCH$_3$ | H | | |
| 31 | 4-OCH$_3$ | H | | |
| 32 | 2-OC$_2$H$_5$ | H | | |
| 33 | 5-O(2-F—C$_6$H$_4$) | H | | |
| 34 | 2-OCOCH$_3$ | H | | |
| 35 | 2-OSO$_2$CH$_3$ | H | | |
| 36 | 5-OSO$_2$(4-CH$_3$—C$_6$H$_4$) | H | | |
| 37 | 2-SCN | H | | |
| 38 | 5-SCN | H | | |
| 39 | 4-SCN | H | | |
| 40 | 2-SCH$_3$ | H | 47 | 7.41 |
| 41 | 5-SCH$_3$ | H | | |
| 42 | 4-SCH$_3$ | H | | |
| 43 | 2-S(O)CH$_3$ | H | | |
| 44 | 2-SO$_2$CH$_3$ | H | | |
| 45 | 4-SO$_2$(CH$_2$)$_3$CH$_3$ | H | | |
| 46 | 2-CHO | H | | |
| 47 | 5-CHO | H | | |
| 48 | 4-CHO | H | | |
| 49 | 2-COCH$_3$ | H | | |
| 50 | 5-COC$_6$H$_5$ | H | | |
| 51 | 2-(E)-CH=NOH | H | | |
| 52 | 5-(E)-CH=NOH | H | | |
| 53 | 4-(E)-CH=NOH | H | | |
| 54 | 2-(E)-CH=NOCH$_3$ | H | | |
| 55 | 2-(E)-C(CH$_3$)=NOH | H | | |
| 56 | 2-CONH$_2$ | H | | |
| 57 | 5-CONH(CH$_3$) | H | | |
| 58 | 4-CON(CH$_3$)$_2$ | H | | |
| 59 | 2-CSNH$_2$ | H | | |
| 60 | 2-CSNH(CH$_3$) | H | | |
| 61 | 2-CH$_3$ | H | gum | 7.48 |
| 62 | 5-CH$_3$ | H | | |
| 63 | 4-CH$_3$ | H | | |
| 64 | 2-C$_2$H$_5$ | H | | |

TABLE I-continued

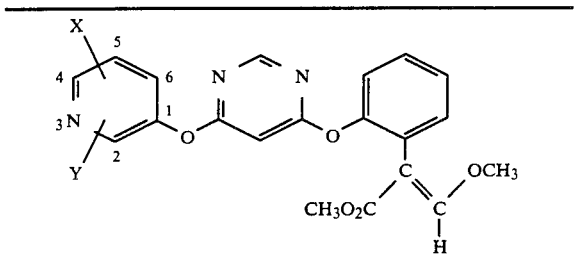

| Compound No. | X | Y | Melting Point (°C.) | Olefinic* |
|---|---|---|---|---|
| 65 | 2-CH₂F | H | | |
| 66 | 2-CH₂Br | H | | |
| 67 | 2-CH₂Cl | H | | |
| 68 | 2-CH₂CN | H | | |
| 69 | 2-CH₂OH | H | | |
| 70 | 2-CH₂OCH₃ | H | | |
| 71 | 2-CH₂OCOCH₃ | H | | |
| 72 | 5-CH₂CN | H | | |
| 73 | 4-CH₂OH | H | | |
| 74 | 5-CH₂OCH₃ | H | | |
| 75 | 2-CH=CH₂ | H | | |
| 76 | 2-CH₂CH=CH₂ | H | | |
| 77 | 2-C≡CH | H | | |
| 78 | 2-CH₂C≡CH | H | | |
| 79 | 5-CH₂C(CH₃)=CH₂ | H | | |
| 80 | 2-OCH₂CH=CH₂ | H | | |
| 81 | 2-OCH₂C≡CH | H | | |
| 82 | 2-C₆H₅ | H | | |
| 83 | 5-C₆H₅ | H | | |
| 84 | 4-C₆H₅ | H | | |
| 85 | 2-OC₆H₅ | H | | |
| 86 | 5-OC₆H₅ | H | | |
| 87 | 4-OC₆H₅ | H | | |
| 88 | 2-(4-Cl—OC₆H₄) | H | | |
| 89 | 2-OCH₂C₆H₅ | H | | |
| 90 | 2-CN | 4-Cl | | |
| 91 | 2-NO₂ | 4-F | | |
| 92 | 2-Cl | 4-Cl | | |
| 93 | 2-OCH₃ | 3-OCH₃ | | |
| 94 | 2-CN | 5-Cl | | |
| 95 | 2-CN | 6-CN | | |
| 96 | 2-F | 5-Cl | | |
| 97 | 5-OCH₃ | 5-OCH₃ | | |
| 98 | 5-CN | 4-F | | |
| 99 | 2-NO₂ | 3-OCH₃ | | |
| 100 | 5-OCH₃ | 5-CN | | |
| 101 | 6-F | H | | |
| 102 | 6-Cl | H | | |
| 103 | 6-Br | H | | |
| 104 | 6-CN | H | | |
| 105 | 6-NO₂ | H | | |
| 106 | 6-NH₂ | H | | |
| 107 | 6-N(CH₃)₂ | H | | |
| 108 | 6-NH.CHO | H | | |
| 109 | 6-NH.CONH₂ | H | | |
| 110 | 6-NH.SO₂CH₃ | H | | |
| 111 | 6-OH | H | | |
| 112 | 6-OCH₃ | H | | |
| 113 | 6-OCOCH₃ | H | | |
| 114 | 6-OSO₂CH₃ | H | | |
| 115 | 6-SCN | H | | |
| 116 | 6-SCH₃ | H | | |
| 117 | 6-S(O)CH₃ | H | | |
| 118 | 6-SO₂CH₃ | H | | |
| 119 | 6-CHO | H | | |
| 120 | 6-COCH₃ | H | | |
| 121 | 6-(E)-CH=NOH | H | | |
| 122 | 6-CONH₂ | H | | |
| 123 | 6-CH₃ | H | | |
| 124 | 6-CH₂Br | H | | |
| 125 | 6-CF₃ | H | | |
| 126 | 6-CH₂CN | H | | |
| 127 | 6-CH₂OCH₃ | H | | |
| 128 | 6-CH₂CH=CH₂ | H | | |
| 129 | 6-OCH₂CH=CH₂ | H | | |
| 130 | 6-C₆H₅ | H | | |

TABLE I-continued

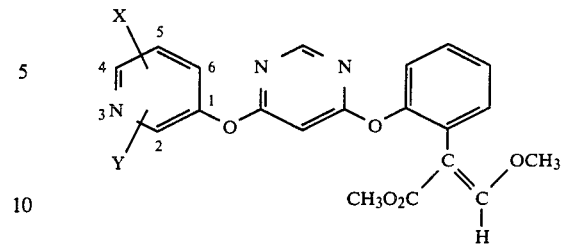

| Compound No. | X | Y | Melting Point (°C.) | Olefinic* |
|---|---|---|---|---|
| 131 | 6-OC₆H₅ | H | | |
| 132 | 3-O(ie.N-oxide) | H | | |
| 133 | 3-O(ie.N-oxide) | Cl | | |
| 134 | 2-F | 6-F | | |

*Chemical shift of singlet from olefinic proton on beta-methoxypropenoate group (ppm tetramethylsilane). Solvent: CDCl₃ unless otherwise stated.

TABLE II

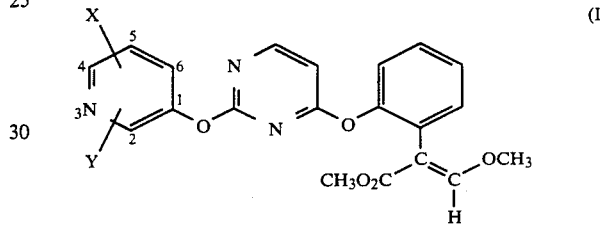

(I)

Table II comprises 134 compounds of the general structure above with all the values of X and Y listed in Table I. That is, compounds numbers 1 to 134 of Table II are the same as those of Table I except that the pyrimidine ring is 4,6-disubstituted in Table I and 2,4-disubstituted in Table II.

TABLE III

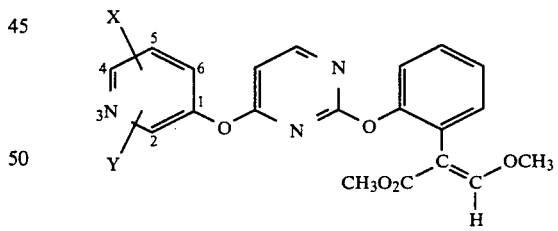

Table III comprises 134 compounds of the general structure above with all the values of X and Y listed in Table I. That is, compounds numbers 1 to 134 of Table III are the same as those of Table I except that the pyrimidine ring is 4,6-disubstituted in Table I and 2,4-disubstituted in Table III.

TABLE IV

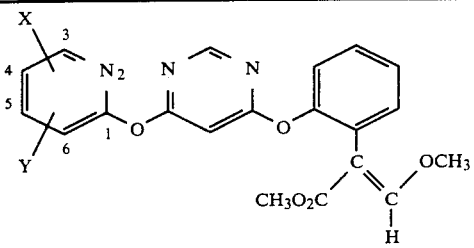

| Compound No. | X | Y | Melting Point (°C.) | Olefinic* |
|---|---|---|---|---|
| 1 | 6-F | H | | |
| 2 | 6-Cl | H | | |
| 3 | 6-Br | H | | |
| 4 | 6-CH$_3$ | H | | |
| 5 | 6-OCH$_3$ | H | | |
| 6 | 6-CN | H | | |
| 7 | 6-NO$_2$ | H | | |
| 8 | 6-OH | H | | |
| 9 | 6-NH$_2$ | H | | |
| 10 | 6-SCH$_3$ | H | | |
| 11 | 6-SO$_2$CH$_3$ | H | | |
| 12 | 5-CH$_3$ | H | | |
| 13 | 5-CF$_3$ | H | | |
| 14 | 4-Cl | H | | |
| 15 | 4-Br | H | | |
| 16 | 4-CF$_3$ | H | | |
| 17 | 4-CH$_3$ | H | | |
| 18 | 3-Cl | H | 75–6 | 7.48 |
| 19 | 3-Br | H | | |
| 20 | 2-O(i.e. N-oxide) | H | | |
| 21 | H | H | Gum | 7.47 |
| 22 | 3-CH$_3$ | H | 89–90 | 7.48 |

*Chemical shift of singlet from olefinic proton on beta-methoxypropenoate group (ppm from tetramethylsilane). Solvent: CDCl$_3$ unless otherwise stated.

TABLE V

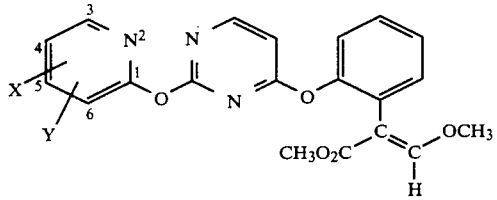

Table V comprises 22 compounds of the general structure above with all the values of X and Y listed in Table IV. That is, compounds numbers 1 to 22 of Table V are the same as those of Table VI except that the pyrimidine ring is 4,6-disubstituted in Table IV and 2,4-disubstituted in Table V.

TABLE VI

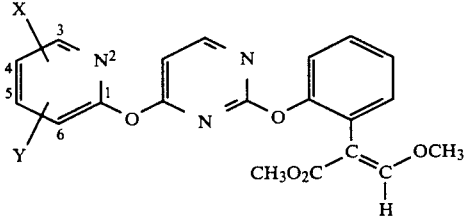

Table VI comprises 22 compounds of the general structure above with all the values of X and Y listed in Table IV. That is, compounds numbers 1 to 22 of Table VI are the same as those of Table IV except that the pyrimidine ring is 4,6-disubstituted in Table IV and 2,4-disubstituted in Table VI.

TABLE VII

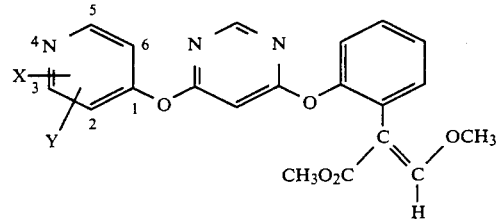

| Compound No. | X | Y | Melting Point (°C.) | Olefinic* |
|---|---|---|---|---|
| 1 | 2-F | H | | |
| 2 | 2-Cl | H | | |
| 3 | 2-Br | H | | |
| 4 | 2-CF$_3$ | H | | |
| 5 | 2-CH$_3$ | H | | |
| 6 | 2-OCH$_3$ | H | | |
| 7 | 2-SCH$_3$ | H | | |
| 8 | 2-CN | H | | |
| 9 | 2-NO$_2$ | H | | |
| 10 | 2-N(CH$_3$)$_2$ | H | | |
| 11 | 3-F | H | | |
| 12 | 3-Cl | H | | |
| 13 | 3-Br | H | | |
| 14 | 3-CF$_3$ | H | | |
| 15 | 3-CH$_3$ | H | | |
| 16 | 3-OCH$_3$ | H | | |
| 17 | 3-SCH$_3$ | H | | |
| 18 | 3-CN | H | | |
| 19 | 3-NO$_2$ | H | | |
| 20 | 2-CN | 3-F | | |
| 21 | 2-F | 6-F | | |

*Chemical shift of singlet from olefinic proton on beta-methoxypropenoate group (ppm from tetramethylsilane). Solvent: CDCl$_3$ unless otherwise stated.

TABLE VIII

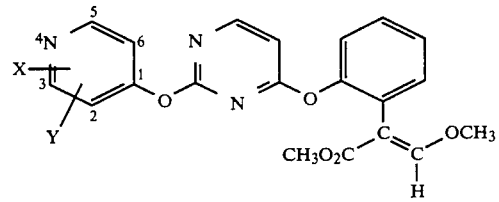

Table VIII comprises 21 compounds of the general structure above with all the values of X and Y listed in Table VII. That is, compounds numbers 1 to 21 of Table VIII are the same as those of Table VII except that the pyrimidine ring is 4,6-disubstituted in Table VII and 2,4-disubstituted in Table VIII.

TABLE IX

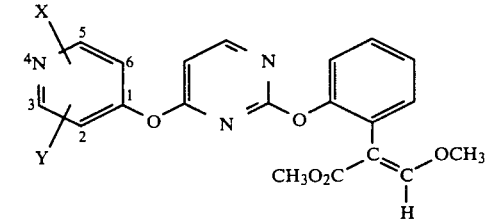

Table IX comprises 21 compounds of the general structure above with all the values of X and Y listed in Table VII. That is, compounds numbers 1 to 21 of Table IX are the same as those of Table VII except that the pyrimidine ring is 4,6-disubstituted in Table VII and 2,4-disubstituted in Table IX.

```
               s = singlet
               d = doublet
               m = multiplet
             ppm = parts per million
```

TABLE X

| Compound No. | Proton NMR data |
| --- | --- |
| 61 (Table I) (270 MHz) | 2.43(3H,s); 3.61(3H,s); 3.77(3H,s); 6.30(1H,s); 7.16–7.57(6H,m); 7.48(1H,s); 8.39(1H,s); 8.45(1H,d) ppm. |
| 21 (Table IV) (270 MHz) | 3.61(3H,s); 3.75(3H,s); 6.44(1H,s); 7.10(1H,d); 7.15–7.45(5H,m); 7.47(1H,s); 7.83(1H,t); 8.37(1H,dd); 8.47(1H,s) ppm. |

The compounds of the invention of formula (I) [equivalent to (IA) when W is the group $CH_3O_2C.C{=}CH.OCH_3$] can be prepared by the steps illustrated in Schemes I and II. Throughout these Schemes the terms X, Y, A, B, G, U, K, L and M are as defined above; W is $CH_3O_2C.C{=}CH.OCH_3$ (or a group that can be transformed into $CH_3O_2C.C{=}CH.OCH_3$ using methods previously described in EP-A-0242081); $Z^1$ and $Z^2$, which may be the same or different, are leaving groups (such as halogen or $CH_3SO_2{-}$), $Z^1$ being the leaving group which is more readily displaced if both $Z^1$ and $Z^2$ are present in the same compound or if $Z^1$ and $Z^2$ are both present in different compounds of a coupling reaction; $T^1$ is hydrogen or a metal (such as sodium); and $T^2$ is hydrogen, a metal (such as sodium) or a protecting group (such as benzyl). Each reaction shown in Schemes I and II is performed either in a suitable solvent or without a solvent, and at a suitable temperature.

Thus compounds of the invention of formula [(IA): W is the group $CH_3O_2C.C{=}CH.OCH_3$] can be prepared by two successive reactions of the Ullmann type, using appropriately functionalised benzene, pyridine and pyrimidine intermediates. The pathways shown in Schemes I and II illustrate that (i) the order of the steps by which these benzene, pyridine and pyrimidine units are assembled can be varied; and (ii) the functional groups which react during the Ullmann coupling, namely an oxygen nucleophile and a leaving group on an aromatic or heteroaromatic ring, may be positioned on either of the substrates at each individual step.

For example, compounds of formula (IA) can be prepared from compounds of formula (II) by treatment with hydroxypyridines of formula (III), wherein $T^1$ is hydrogen, in the presence of a base (such as potassium carbonate). Alternatively, compounds of formula (IA) can be prepared from compounds of formula (II) by treatment with pyridyloxy salts of formula (III), wherein $T^1$ is a metal (such as sodium). When hydroxypyridines of formula (III) are 2- or 4-hydroxypyridines (which may exist mainly as the corresponding pyridone tautomers), reaction conditions (e.g. base, solvent) are chosen to optimise the formation of the required O-linked product of formula (I) (that is, to minimise the formation of the alternative N-linked product).

Compounds of formula (II) can be prepared by treatment of compounds of formula (IV) with phenols of formula (V), wherein $T^1$ is hydrogen, in the presence of a base (such as potassium carbonate). Alternatively, compounds of formula (II) can be prepared by treatment of compounds of formula (IV) with phenolate salts of formula (V), wherein $T^1$ is a metal (such as sodium). Similarly, compounds of formula (II) can be prepared by allowing compounds of formula (VI) to react with compounds of formula (VII); when $T^1$ is hydrogen, the reaction is performed in the presence of a base (such as potassium carbonate).

The preparation of compounds of formula (IA) from intermediates (VIII), (XI) and (XII), as well as the preparation of these intermediates from the monocyclic precursors, is carried out by similar methods.

Modifications to the group W may be made at any appropriate stage in the pathways shown in Schemes I and II. For example, during one or more of the Ullmann couplings, W may be the group $CH_2CO_2R$ (wherein R is H, $CH_3$ or a metal) to be converted at the last stages of the synthesis into the group $CH_3O_2C.C{=}CH.OCH_3$ using, for example, one of the methods described in EP-A-0242081. When $T^2$ is a protecting group, it may be removed at any appropriate reaction step.

The substituents X, Y, A, B, E (one of K, L and M having the value CE, wherein E is as defined above), G and U may also be modified at any appropriate reaction step. For example, if X is $NO_2$ it may be converted via reduction and diazotisation into a halogen, CN or OH group, and this may be carried out on intermediates such as (XI) or (XII) or on the compounds of formula (IA). Or, for example, if G is a halogen such as chlorine, it may be removed at an appropriate stage of the synthesis (such as at the last stage) to give the corresponding pyrimidine in which G is hydrogen. N-Oxides and N-alkyl pyridinium salts can be made by N-oxidation or quaternisation, respectively, of appropriate intermediates or of the final compounds of the invention of formula (I).

The intermediates of formulae (II) and (VIII) may be interconverted using standard methods. The intermediates of formulae (XI) and (XII) are similarly interconvertible. Compounds of formulae (III), (IV), (VI), (IX), (X), (XIII), (XIV), (XV), (XVI) and (XVII) can be prepared by standard methods described in the chemical literature. Compounds of formulae (V) and (VII) can either be prepared by standard methods described in the chemical literature, or, when W is $CH_3O_2C.C{=}CH.OCH_3$, can be prepared by methods described in EP-A-0242081 and EP-A-0178826 respectively.

Scheme I

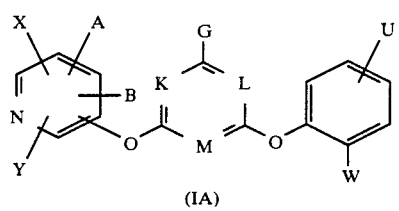

(IA)

5,059,605
-continued
Scheme I
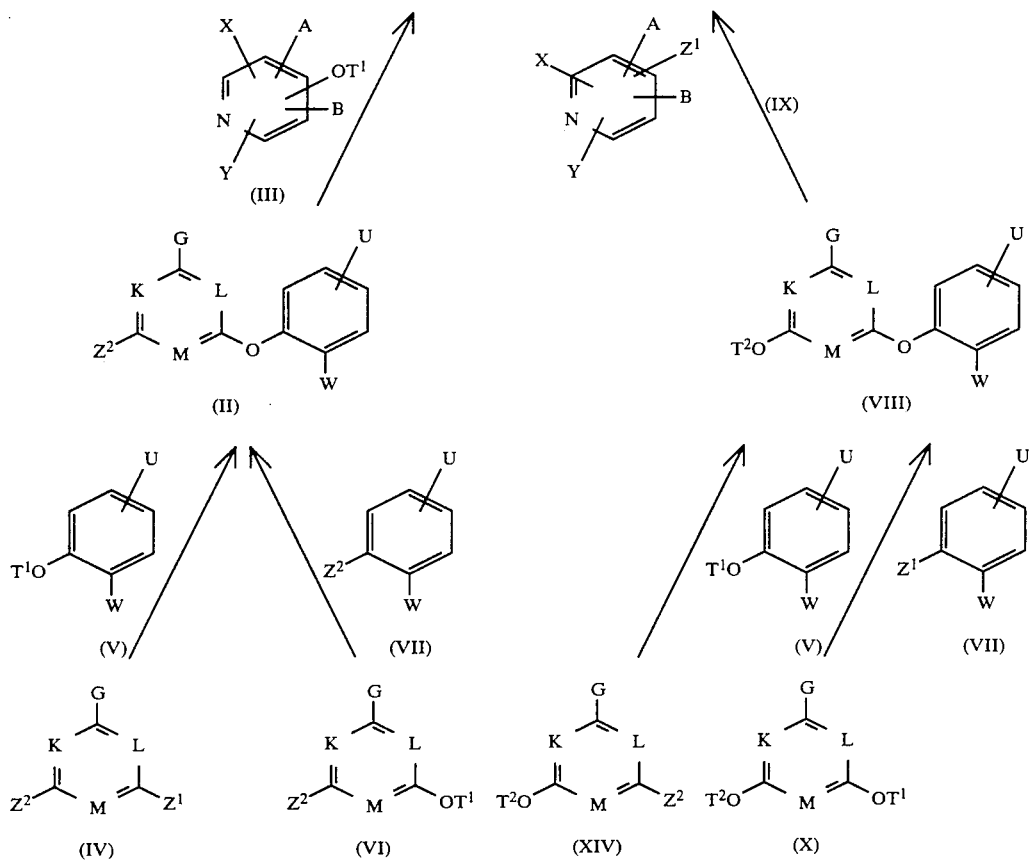
Scheme II
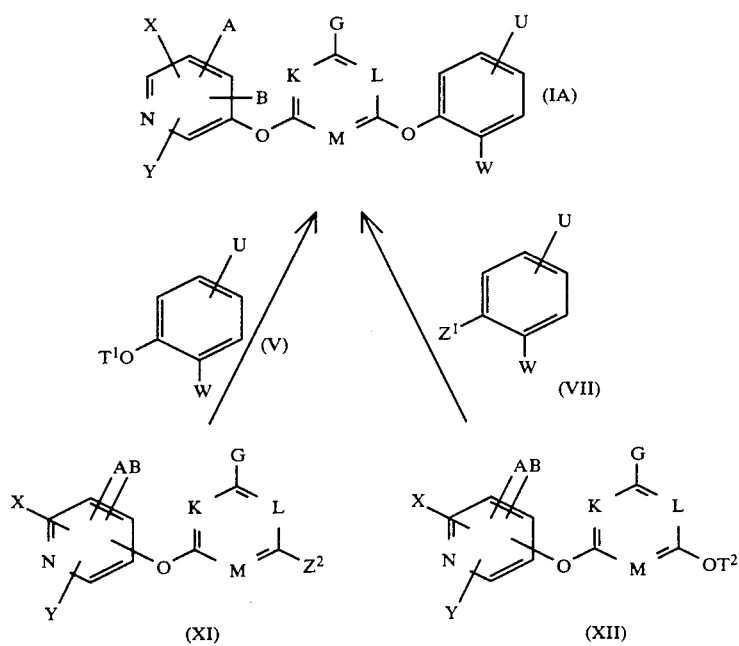

Scheme II

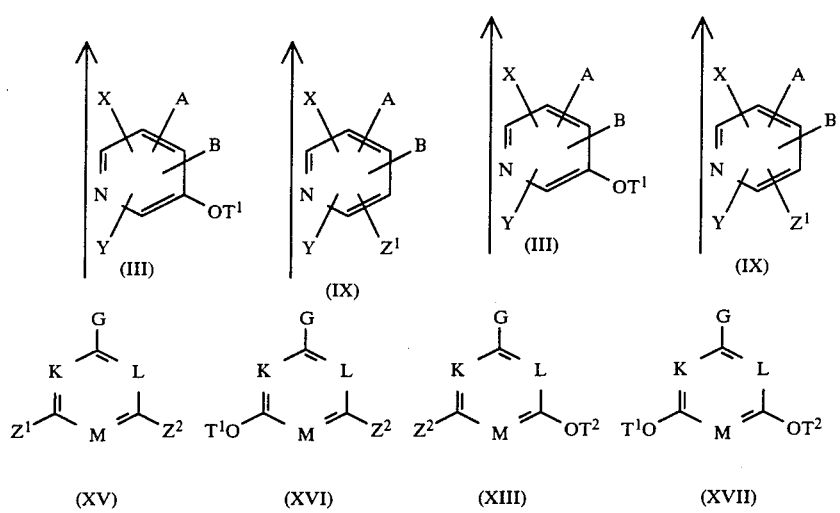

In a further aspect, the invention provides processes as herein described for preparing the compounds of the invention.

The compounds of the invention are active fungicides and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

Helminthosporium spp., Rhynchosporium spp., Septoria spp., *Pseudocercosporella herpotrichoides* and *Gaeumannomyces graminis* on cereals.

*Cercospora arachidicola* and *Cercosporidium personata* on peanuts and other Cercospora species on other hosts, for example, sugar beet, bananas, soya beans and rice.

*Botrytis cinerea* (grey mould) on tomatoes, strawberries, vegetables, vines and other hosts.

Alternaria species on vegetables (e.g. cucumber), oil-seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts.

*Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botryti cinerea* on grapes).

Further, some of the compounds may be active a: seed dressings against Fusarium spp., Septoria spp. Tilletia spp., (bunt, a seed-borne disease of wheat), Usti lago spp. and Helminthosporium spp. on cereals, *Rhi zoctonia solani* on cotton and *Pyricularia oryzae* on rice The compounds may move acropetally/locally ir plant tissue. Moreover, the compounds may be volatilε enough to be active in the vapour phase against fungi or the plant.

The invention therefore provides a method of com bating fungi which comprises applying to a plant, to ε seed of a plant or to the locus of the plant or seed ε fungicidally effective amount of a compound as herein before defined, or a composition containing the same.

The compounds may be used directly for agricultura purposes but are more conveniently formulated intc compositions using a carrier or diluent. The inventior thus provides fungicidal compositions comprising ε compound as hereinbefore defined and an acceptablε carrier or diluent therefor.

The compounds can be applied in a number of ways For example, they can be applied, formulated or unfor mulated, directly to the foliage of a plant, to seeds or tc other medium in which plants are growing or are to bε planted, or they can be sprayed on, dusted on or appliec as a cream or paste formulation, or they can be appliec as a vapour or as slow release granules.

Application can be to any part of the plant including the foliage, stems, branches or roots, or to soil surround ing the roots, or to the seed before it is planted, or to thε soil generally, to paddy water or to hydroponic culturε systems. The invention compounds may also be injectec into plants or sprayed onto vegetation using electrody namic spraying techniques or other low volume meth ods.

The term "plant" as used herein includes seedlings bushes and trees. Furthermore, the fungicidal methoc of the invention includes preventative, protectant, pro phylactic and eradicant treatments.

The compounds are preferably used for agricultura: and horticultural purposes in the form of a composition. The type of composition used in any instance will de pend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitable contain up to 25% by weight of he compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4 -(4-chlorophenyl)-2-phenyl-2-(1H-1,2,4-triazol-1-ylmethyl)-butyronitrile, (Z)-N-but-2-enyloxymethyl-2-chloro-2',6'-diethylacetanilide, 1-(2-cyano-2-methoxyiminoacetyl)-3-ethyl urea, 1-[(2RS,4RS;2RS,4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)-quinazolin-4(3H)-one, 3-chloro-4-[4-methyl-2-(1H-1,2,4-triazol-1-methyl)-1,3-dioxolan-2-yl]phenyl-4-chlorophenyl ether, 3-chloro-5-ethylsulphinylthiophene-2,4-dicarbonitrile, 4-bromo-2-cyano-N,N-dimethyl-6-trifluoromethylbenzimidazole-1-sulphonamide, 5-ethyl-5,8-dihydro-8-oxo(1,3) -dioxolo(4,5-g)quinoline-7-carboxylic acid, α-[N-(3-chloro-2,6-xylyl)-2-methoxyacetamido]-γ-butyrolactone, anilazine, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl (methylthioethylideneamino-oxycarbonyl)amino]-thio)-β-alaninate, etridiazole, fenapanil, fenarimol, fenfuram, fenpiclonil, fenpropidin, fenpropimorph, fentin acetate, fentin hydroxide, flutolanil, flutriafol, fluzilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, tetraconazole, thiabendazole, thiophanate-methyl, thiram, tolclofos-methyl, triacetate salt of 1,1'-iminodi(octamethylene)-diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophas, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl) -4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. In the Examples, the term 'ether' refers to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption in all cases. $^1$H NMR spectra were recorded using $CDCl_3$-solutions. The following abbreviations are used:

| | |
|---|---|
| DMSO = | dimethylsulphoxide |
| DMF = | N,N-dimethylformamide |
| NMR = | nuclear magnetic resonance |
| IR = | infrared |
| GC = | Gas chromatography |
| s = | singlet |
| d = | doublet |
| m = | multiplet |
| mp = | metling point |
| ppm = | parts per million |

EXAMPLE 1

This example illustrates the preparation of (E)-methyl 2-[2-(6-(2-chloropyrid-3-yloxy)pyrimidin-4-yloxy)-phenyl]-3-methoxypropenoate (compound No. 5 of Table I).

To a solution of 4,6-dichloropyrimidine (0.76g, 5.10mmol) in dry DMF (4ml) at 0° C. was added anhydrous potassium carbonate (0.70g, 5.10mmol). A solution of (E)-methyl 2-(2-hydroxyphenyl)-3-methoxypropenoate (0.53g, 2.55mmol, prepared as described in Example 3 of EP-A-0242081) in dry DMF (2ml) was then added dropwise with stirring. After the addition was complete, the reaction mixture was allowed to warm to room temperature and stirring was continued over the weekend. The reaction mixture was then diluted with water (15ml) and extracted with ether (3×20ml). The combined ether extracts were washed with brine and dried. Evaporation afforded a brown liquid (1.10g) which was chromatographed (eluent ether:n-hexane, 3:2) to give (E)-methyl 2-[2-(6-chloropyrimidin-4-yloxy)phenyl]-3-methoxypropenoate as a thick, pale yellow oil (0.58, 71%) which crystallised on standing. Recrystallisation from ether/dichloromethane (trace)/n-hexane at -78° C. gave the product as a white powder (0.25g), mp 94°-5° C. In a separate preparation, 15g of product was obtained from 4,5-dichloropyrimidine (15.90g), (E)-methyl 2-(2-hydroxyphenyl)-3-methoxypropenoate (14.80g) and anhydrous potassium carbonate (19.64g).

(E)-Methyl 2-[2-(6-chloropyrimidin-4-yloxy)phenyl]-3-methoxypropenoate (0.50g, 1.56mmol) was heated for 10.5 hours at 95° C. with 2-chloro-3-hydroxypyridine (0.22g, 1.72mmol) and potassium carbonate (0.24g, 1.72mmol) in DMF (20ml) in the presence of a catalytic amount of copper(I) chloride. The reaction mixture was cooled, diluted with water and then extracted with ether. The combined ether layers were washed with 2M sodium hydroxide solution and brine and then dried. Evaporation of the solvent gave a pale yellow oil (0.67g). Chromatography (eluent ether:n-hexane, 7:1) gave a white foam (0.55g). Trituration with ether/dichloromethane/n-hexane gave the title compound as a white solid (0.45g, 70%), mp 104°-5° C.; $^1$H NMR (270MHz): δ3.63(3H,s); 3.76 (3H,s); 6.39 (1H,s); 7.18–7.71 (6H,m); 7.49 (1H,s); 8.33 (1H,m); 8.36 (1H,s) ppm.

EXAMPLE 2

This example illustrates the preparation of (E)-methyl 2-[2-(6-(6-chloropyrid-2-yloxy)pyrimidin-4-yloxy)-phenyl]-3-methoxypropenoate (compound No. 18 of Table IV).

A stirred mixture containing (E)-methyl 2-[2-(6-chloropyrimidin-4-yloxy)phenyl]-3-methoxypropenoate (0.75g, 2.34 mmol, prepared as described in Example 1), anhydrous potassium carbonate (0.35g, 2.57 mmol), 6-chloropyrid-2-one (0.33g, 2.57 mmol) and a catalytic amount of copper(I) chloride in DMF (25ml) was heated at 95° C. for 90 minutes and then overnight at 100° C. Work up as in Example 1 gave a pale yellow oil (0.70g), which was chromatographed (eluent diethyl ether-hexane, 7:1) to afford a thick colourless oil (0.34g). Crystallisation from ether/hexane then gave the title compound as a white solid (0.25g, 26%); mp 75°-6° C.; infrared max 1712, 1643 cm$^{-1}$; mass spectrum m/e 413(M+); $^1$H NMR (270MHz): δ 3.63(3H,s), 3.75(3H,s); 6.47(1H,s); 7.05(1H,d); 7.17–7.47(5H,m); 7.48(1H,s); 7.78(1H,t); 8.47(1H,s) ppm.

The following are examples of compositions suitable for agricultural and horticultural purposes which can be formulated from the compounds of the invention. Such compositions form another aspect of the invention. Percentages are by weight.

EXAMPLE 3

An emulsion concentrate is made up by mixing and stirring the ingredients until all are dissolved.

| Compound No. 1 of Table I | 10% |
| --- | --- |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 4

The active ingredient is dissolved in methylene dichloride and the resultant liquid sprayed on to the granules of attapulgite clay. The solvent is then allowed to evaporate to produce a granular composition.

| Compound No. 1 of Table I | 5% |
| --- | --- |
| Attapulgite granules | 95% |

EXAMPLE 5

A composition suitable for use as a seed dressing is prepared by grinding and mixing the three ingredients.

| Compounds No. 1 of Table I | 50% |
| --- | --- |
| Mineral oil | 2% |
| China clay | 48% |

EXAMPLE 6

A dustable power is prepared by grinding the mixing the active ingredient with talc.

| Compound No. 1 of Table I | 5% |
| --- | --- |
| Talc | 95% |

EXAMPLE 7

A suspension concentrate is prepared by ball milling the ingredients to form an aqueous suspension of the ground mixture with water.

| Compound No. 1 of Table I | 40% |
| --- | --- |
| Sodium lignosulphonate | 10% |
| Bentonite clay | 1% |
| Water | 49% |

This formulation can be used as a spray by diluting into water or applied directly to seed.

EXAMPLE 8

A wettable powder formulation is made by mixing together and grinding the ingredients until all are thoroughly mixed.

| Compound No.1 of Table I | 25% |
| --- | --- |
| Sodium lauryl sulphate | 2% |
| Sodium lignosulphonate | 5% |
| Silica | 25% |
| China clay | 43% |

EXAMPLE 9

The compounds were tested against a variety of foliar fungal diseases of plants. The technique employed was as follows.

The plants were grown in John Innes Potting Compost (No 1 or 2) in 4cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

| |
|---|
| 4 = no disease |
| 3 = trace-5% of disease on untreated plants |
| 2 = 6-25% of disease on untreated plants |
| 1 = 26-59% of disease on untreated plants |
| 0 = 60-100% of disease on untreated plants |

The results are shown in Table XI.

TABLE XI

| COMPOUND NO | TABLE NO | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS LYCOPERSICI (TOMATO) |
|---|---|---|---|---|---|---|---|---|
| 1 | I | 4 | 3 | 4 | 4 | 4 | 4 | 4 |
| 5 | I | 4 | 4 | 4 | 4 | 4 | 4 | 4 |
| 8 | I | 3$^a$ | 3$^a$ | 3$^a$ | 3$^a$ | — | 4$^a$ | 3$^a$ |
| 13 | I | 4 | 4 | 0 | 3 | 4 | 4 | 4 |
| 18 | IV | 4 | 4 | 4 | 4 | 4 | 4 | 4 |
| 21 | IV | 4$^a$ | 4$^a$ | 4$^a$ | 3$^a$ | — | 3$^a$ | 0$^a$ |
| 22 | IV | 4 | 4 | 4 | 4 | — | 4 | 4 |
| 40 | I | 4 | 4 | 4 | 3 | 4 | 4 | 4 |
| 61 | I | 4 | 4 | 4 | 4 | 4 | 4 | 3 |

$^a$ = 10 ppm foliar application only
— = no result

We claim:

1. Compounds having the formula (I):

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C:CH.OCH_3$, 1-(imidazol-1-yl)vinyl, a 5-membered heterocyclic ring containing one, tow or three nitrogen heteroatoms; pyridopyridazines, pyridopyrimidines, pyridooxazines, pyrrolo-, furo-, thieno-, triazolo-, and thiadiazolopyridines; A, B, E, G, and U are independently hydrogen, halogen $C_{1-4}$ alkyl, $C_{1-4}$ alkoxy, cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one or more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano; and their pyridine N-oxides and N-alkyl pyridinium salts.

2. Compounds according to claim 1 in which any two of K, L and M are nitrogen and the other is CH; A, B, G and U are all hydrogen; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $NR^1R^2$, $NHCOR^1$, $NHCONR^1R^2$, $NHSO_2R^1$, $OR^1$, $OCOR^1$, $OSO_2R^1$, $SR^1$, $SOR^1$, $SO_2R^1$, $COR^1$, $CR^1=NOR^2$, $CO_2R^1$, $CONR^1R^2$, $CSNR^1R^2$; and R and $R^2$ are independently hydrogen, $C_{1-4}$ alkyl o phenyl; the aliphatic moieties of any of the foregoing being optionally substituted with one or more of halogen, cyano, $OR^1$ or $OCOR^1$ and the phenyl moieties of any of the foregoing being optionally substituted with one or more of halogen, $C_{1-4}$ alkyl, $C_{1-4}$ alkoxy, nitro or cyano; and their pyridine N-oxides and N-alkyl pyridinium salts.

3. Compounds according to claim 1 in which any two of K, L and M are nitrogen and the other is CH; A, B G and U are all hydrogen; X, which is attached to the pyridine ring at the position adjacent to the oxygen link is hydrogen, halogen, $C_{1-4}$ alkyl, $C_{1-4}$ alkyl, substituted with halogen, hydroxy, cyano, $C_{1-4}$ alkoxy, or $C_{1-4}$ alkanoyloxy, $C_{2-4}$ alkenyl, $C_{2-4}$ alkynyl, $C_{2-4}$ alkenyloxy, $C_{2-4}$ alkynyloxy, phenyl, benzyloxy, cyano, isocyano isothiocyanato, nitro, amino, mono- or di($C_{1-4}$)alkylamino, formylamino, $C_{1-4}$ alkanoylamino, benzylamino, ureido, phenylureido, $C_{1-4}$ alkylsulphonylamino, phenylsulphonylamino, hydroxy, $C_{1-4}$ alkoxy, phenoxy, $C_{1-4}$ alkanoyloxy, $C_{1-4}$ alkylsulphonyloxy, phenylsulphonyloxy, $C_{1-4}$ alkylthio, $C_{1-4}$ alkylsulphinyl, $C_{1-4}$ alkylsulphonyl, formyl, $C_{1-4}$ alkanoyl, benzoyl, hydroxyimino($C_{1-4}$)alkyl, $C_{1-4}$ alkoxyimino($C_{1-4}$)alkyl, carbamoyl, $C_{1-4}$ alkylcarbamoyl, thiocarbamoyl or $C_{1-4}$ alkylthiocarbamoyl, the phenyl ring of any of the foregoing being optionally substituted with halogen, $C_{1-4}$ alkyl, $C_{1-4}$ alkoxy, nitro or cyano: and Y is halogen, $C_{1-4}$ alkyl, $C_{1-4}$ alkoxy, nitro, cyano or hydrogen.

4. Compounds according to claim 2 in which X is attached to the pyridine ring at the position adjacent to the oxygen link.

5. Compounds according to any one of claims 1 to 3 in which K and L are both nitrogen and M is CH.

6. Compounds having the formula (I.1):

in which X is hydrogen, halogen, $C_{1-4}$ alkyl, $C_{1-4}$ alkoxy, $C_{1-4}$ alkylthio, trifluoromethyl, trifluoromethoxy, cyano or nitro.

7. Compounds having the formula (I.2):

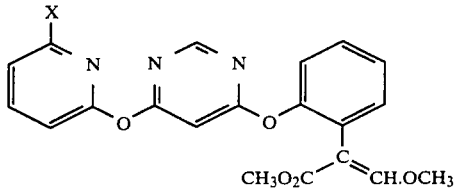

(I.2)

in which X is hydrogen, halogen, $C_{1-4}$ alkyl, $C_{1-4}$ alkoxy, $C_{1-4}$ alkylthio, trifluoromethyl, trifluoromethoxy, cyano or nitro.

8. A fungicidal composition comprising a fungicidally effective amount of a compound according to claim 1 and a fungicidally acceptable carrier or diluent therefor.

9. A method of combating fungi which comprises applying to plants, to the seeds of plants or to the locus of the plants or seeds, an effective amount of a compound according to claim 1 or a composition according to claim 8.

* * * * *

UNITED STATES PATENT AND TRADEMARK OFFICE
CERTIFICATE OF CORRECTION

PATENT NO. : 5,059,605
DATED : October 22, 1991
INVENTOR(S) : Clough, et. al.

It is certified that error appears in the above-indentified patent and that said Letters Patent is hereby corrected as shown below:

Claim 1, column 21, line 52, change "tow" to --two--.

Claim 1, column 21, line 52, following "heteroatoms"; insert --or X and Y, when ortho to one another, together form a methylenedioxy group or together with the pyridine ring to which they are attached form a ring system selected from the group consisting of quinolines, isoquinolines, naphthyridines, pyranopyridines, pyridopyranzines,--

Claim 2, column 21, line 53, change "pyridopyrimidiens" to --pyridopyrimidines--.

Signed and Sealed this

Twentieth Day of September, 1994

Attest:

BRUCE LEHMAN

Attesting Officer

Commissioner of Patents and Trademarks